US008673884B2

(12) United States Patent
Jones et al.

(10) Patent No.: US 8,673,884 B2
(45) Date of Patent: Mar. 18, 2014

(54) ANTI-INFLUENZA COMPOUNDS (75) Inventors: Steven J. Jones, Burnaby (CA); Allan Sik-Yin Lau, Hong Kong (CN); Jianghong An, Vancouver (CA); Hing Yee Law, Hong Kong (CN); Chun Wai Davy Lee, Hong Kong (CN); Lit Man Poon, Hong Kong (CN)

(73) Assignees: Versitech Limited, Hong Kong (CN); British Columbia Cancer Agency Branch, Vancouver, British Columbia (CA)

( * ) Notice: Subject to any disclaimer, the term of this patent is extended or adjusted under 35 U.S.C. 154(b) by 376 days.

(21) Appl. No.: 12/866,118

(22) PCT Filed: Feb. 4, 2009

(86) PCT No.: PCT/CA2009/000133
§ 371 (c)(1),
(2), (4) Date: Aug. 4, 2010

(87) PCT Pub. No.: WO2009/097682
PCT Pub. Date: Aug. 13, 2009

(65) Prior Publication Data
US 2011/0009369 A1 Jan. 13, 2011

Related U.S. Application Data (60) Provisional application No. 61/026,167, filed on Feb. 5, 2008.

(51) Int. Cl.
C07D 239/46 (2006.01)
A61K 31/13 (2006.01)
A61K 31/215 (2006.01)

(52) U.S. Cl.
USPC .............. 514/86; 514/272; 544/243; 544/321

(58) Field of Classification Search
USPC ............................. 544/243, 321; 514/86, 272
See application file for complete search history.

(56) References Cited

U.S. PATENT DOCUMENTS 6,583,309 B1 * 6/2003 Rana et al. ....................... 560/24
6,777,420 B2 * 8/2004 Zhi et al. ....................... 514/272

FOREIGN PATENT DOCUMENTS

WO    WO 93/13079    *  7/1993
WO    2007141516       12/2007

OTHER PUBLICATIONS

B. Muller et al., Antiviral Strategies in, Antiviral Strategies 1-24, 7 (H.-G. Krausslich et al., eds., 2009).*
N.E. Sharpless et al., Nature Reviews Drug Discovery 1-14, 2 (2006).*

J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
P.D. Griffiths, Cytomegalovirus in, Principles and Practice of Clinical Virology 85-122 (A.J. Zuckerman et al., eds, 5th ed., 2001).*
Reddy, Responding to pandemic (H1N1) 2009 influenza: the role of oseltamivir, Journal of Antimicrobial Chemotherapy, 65 Suppl 2, pp. ii35-ii40 (2010).*
Mizumoto et al., Effetiveness of antivira prophylaxis coupled with contact tracing in reducing the transmission of the influenza A (H1N1-2009): a systemic review, Theoritical Biology and Medical Modelling, 10:4, pp. 1-18 (2013).*
Baker et al., "Analogs of Tetrahydrofolic Acid, XVII. On the Mode of Binding of the p-Aminobenzoyl Moiety of N-(2-Amino-4-hydroxy-6-methyl-5-pyrimidylpropyl)-p-aminobenzoyl-L-glutamic Acid to Dihydrofolic Reductase", Journal of Med. Chem., vol. 8, Jan. 1965, pp. 35-41.
Sun et al., "Synthesis and evaluation of a new series of substituted acyl(thio)urea and thiadiazolo [2-3-alpha] pyrimidine derivatives as poten inhibitors of influenza virus neuramindease", Bioorganic & Medicinal Chemistry, available online Sep. 18, 2006, No. 14, pp. 8574-8581.
Ye et al., "The mechanism by which influenza A virus nucleoprotein forms oligomers and binds RNA", Nature, Dec. 21/28, 2006, 444: pp. 1078-1082.
Bulletin of the World Health Organization, "A revision of the system of nomenclature for influenza viruses: a WHO memorandum", No. 58(4). Feb. 1980, p. 585-591.
Russell et al., "The structure of H5N1 avian influenza neuraminidase suggests new opportunities for drug design", Nature, Sep. 7, 2006, No. 443, pp. 45-49.
World Health Organization Global Influenza Program Surveillance Network, "Evolution of H5N1 avian influenza viruses in Asia", Emerging Infectious Diseases, vol. 11, No. 10, Oct. 2005, pp. 1515-1521.
de Jong et al., "Fatal outcome of human influenza A (H5N1) is associated with high viral load and hypercytokinemia", Nat. med., vol. 12, No. 10, Oct. 2006, pp. 1203-1207.

(Continued)

Primary Examiner — Deepak Rao
(74) Attorney, Agent, or Firm — Gail C. Silver; Borden Ladner Gervais LLP (57) ABSTRACT The present invention provides pyrimidinyl compounds of formula (I) and pharmaceutically acceptable salts thereof. These compounds may be used for the inhibition of influenza. In particular, the compounds of the invention may be used for the treatment or prophylaxis of influenza A, most particularly H1N1 or H5N1 influenza. The compounds of the invention can also be used for the treatment or prophylaxis of a disease caused by *Vibrio cholerae, Clostridium perfringens, Streptococcus pneumoniae, Arthrobacter sialophilus*, an orthomyxovirus, a paramyxovirus, a parainfluenza virus, mumps virus, Newcastle disease virus, fowl plague virus or Sendai virus.

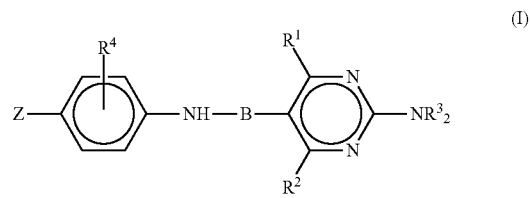

24 Claims, 2 Drawing Sheets

(56) References Cited

OTHER PUBLICATIONS

Moscona, "Oseltamivir resistance-disabling our influenza defences", The New England Journal of Medicine, Dec. 22, 2005, vol. 353, No. 25, pp. 2633-2636.

Beigel et al., "Avian influenza A (H5N1) infection in humans", New England Journal of Medicine, No. 353. Sep. 29, 2005, vol. 353, No. 13, pp. 1374-1385.

de Jong et al., "Oseltamivir resistance during treatment of influenza A (H5N1) infections", New England Journal of Medicine, vol. 353, No. 25, Dec. 22, 2005, pp. 2667-2672.

Abagyan et al., "Biased probability Monte Carlo conformationals searches and electrostatic calculations for peptides and proteins", J. Mol. Biol. No. 235, 1994, pp. 983-1002.

\* cited by examiner

ANTI-INFLUENZA COMPOUNDS

CROSS-REFERENCE TO RELATED APPLICATIONS

This application is a U.S. National Entry of PCT Patent Application No. PCT/CA2009/000133, filed Feb. 4, 2009, which claims the benefit of priority of U.S. Patent Application Ser. No. 61/026,167, filed Feb. 5, 2008.

FIELD OF THE INVENTION

This invention relates to compounds for the treatment of influenza.

BACKGROUND OF THE INVENTION

The impact of influenza infection is felt globally each year when the disease develops in approximately 20% of the world's population. Influenza A virus, in particular, represents a significant health risk to the public. This is due both to its ability to spread quickly within human populations and the high degree of mortality associated with infection. In the last century, three influenza A pandemics in 1918, 1957 and 1968 killed cumulatively over 50 million people. The highly pathogenic H5N1 strain of influenza A virus is emerging as the most likely cause of the world's next major influenza pandemic.

Influenza viruses belong to the family Orthomyxoviridae, and are divided into three (3) genera: Influenza A, Influenza B, and Influenza C. Influenza A can cause of epidemics and pandemics in humans and may be transmitted through an avian intermediate host. Influenza B can causes epidemics and has no intermediate host. Influenza C does not occur in epidemics and causes mild disease.

Influenza A viruses are further classified based on the identity of two surface glycoproteins: hemagglutinin and neuraminidase. Nine subtypes of influenza neuraminidases are known, N1 to N9, and sixteen subtypes of hemagglutinin are known, H1 to H16. Thus, influenza A H5N1 refers to an influenza virus which contains H5 subtype hemagglutinin and N1 subtype neuraminidase.

Neuraminidase cleaves the specifc linkage of the sialic acid receptor in the cell membrane, resulting in the release of the newly formed virions from the infected cells. In addition, neuraminidase may function to facilitate the early process of influenza virus infection of lung epithelial cells. Hence, neuraminidase inhibitors have been an attractive target for the development of novel anti-influenza drugs. Use of effective neuraminidase inhibitors can serve an important role in the early containment of influenza outbreaks in the human population and would complement widespread use of new avian influenza vaccines. Influenza neuraminidases are classified within two categories: group-1 and group-2. Group-1 contains N1, N4, N5, and N8 subtypes, and group-2 contains N2, N3, N6, N7, and N9.

Existing influenza medicines include oseltamivir (Tamiflu®) and zanamivir (Relenza). These function by inhibiting neuraminidase. However, there have been several documented cases of the emergence of resistance to these drugs by several different sub-strains of avian flu H5N1. Also, the FDA has recently issued a warning label for Tamiflu® after reports of serious psychiatric side-effects in patients receiving the drug, especially children. These factors suggest that there is a significant clinical need for new influenza drugs, particularly to contain the avian flu virus strain H5N1, with improved properties (including efficacy, selectivity and reduced sensitivity to resistance) relative to the current marketed drugs.

SUMMARY OF THE INVENTION

In one aspect, the present invention provides a compound of formula (I)

$$Z-\underset{R^4}{\bigcirc}-NH-B-\underset{R^2}{\bigcirc}-NR^3_2 \quad (I)$$

wherein
Z is —CH=CHC(=O)Y, —CH=CHS(=O)Y, —CH=CHP(=O)Y$_2$, —OP(=O)(OH)$_2$, or heterocyclyl, where each Y is independently acyl, alkyl, haloalkyl, hydroxyl, hydroxyalkyl, amino, or alkylamino;
$R^1$ and $R^2$ are independently hydroxyl, alkyl, amino, alkylamino, acyl, or hydroxylalkyl,
B is alkylene or substituted alkylene, wherein the substituents are —H, —COOH, acyl, —NO, or alkylamino;
each $R^3$ is independently —H or alkyl; and
$R^4$ is —H, acyl, amino, alkylamino, or —COOH;
and pharmaceutically acceptable salts thereof.

In one aspect, the invention also encompasses uses of said compounds for the inhibition of influenza. In one embodiment, compounds of the invention may be used for the treatment or prophylaxis of influenza A, in particular H1N1 or H5N1 influenza.

DETAILED DESCRIPTION OF THE INVENTION

Compounds:

In one aspect, the present invention provides a compound of formula (I)

$$Z-\underset{R^4}{\bigcirc}-NH-B-\underset{R^2}{\bigcirc}-NR^3_2 \quad (I)$$

wherein
Z is —CH=CHC(=O)Y, —CH=CHS(=O)Y, —CH=CHP(=O)Y$_2$, —OP(=O)(OH)$_2$, or heterocyclyl, where each Y is independently acyl, alkyl, haloalkyl, hydroxyl, hydroxyalkyl, amino, or alkylamino;

$R^1$ and $R^2$ are independently hydroxyl, alkyl, amino, alkylamino, acyl, or hydroxylalkyl,

B is alkylene or substituted alkylene, wherein the substituents are —H, —COOH, acyl, —NO, or alkylamino;

each $R^3$ is independently H or alkyl; and $R^4$ is H, acyl, amino, alkylamino, or —COOH;

and pharmaceutically acceptable salts thereof.

In one aspect, the present invention provides compounds of formula (Ia)

(Ia)

wherein

Z is —CH=CHCOCH$_2$Cl, —CH=CHCOCH$_2$CH$_3$, —CH=CHCOOH, —CH=CHCONH$_2$, —CH=CHCONHCH$_3$, —CH=CHCOCOH, —CH=CHS(=O)OH, —CH=CHP(=O)(OH)$_2$, —OP(=O)(OH)$_2$, or 2-pyrrolidinone-5-yl;

$R^1$ and $R^2$ are independently —OH, —CH$_3$, —NH$_2$, —COH, or —CH(OH)$_2$, $R^3$ is —COH, —NO, or —H; and $R^4$ is —COOH, —COH, COCH$_3$, COCH$_2$CH$_3$, —N(CH$_3$)$_2$, or —H;

and pharmaceutically acceptable salts, solvents, and hydrates thereof.

Examples of such compounds are shown in Table 2.

The compound 4-(4-((3-(2-amino-4-hydroxy-6-methyl-5-pyrimidinyl)propyl)amino)phenyl)-1-chloro-3-buten-2-one is previously known from Baker, B R and Jordaan, J H, *J. Med. Chem.* 1965 Jan (8): 35-41, and was reported therein to be an inhibitor of dihydrofolic reductase. However, its use for treating influenza is novel.

"Acyl" means a radical —C(O)R where R is hydrogen or alkyl. Examples include formyl, acetyl, ethylcarbonyl, and the like.

"Alkyl" means a linear saturated monovalent hydrocarbon radical of one to eight carbon atoms or a branched saturated monovalent hydrocarbon radical of three to eight carbon atoms. It may include a linear monovalent hydrocarbon radical of one to four or one to three carbon atoms. Examples include methyl, ethyl, propyl, 2-propyl, n-butyl, iso-butyl, tert-butyl, pentyl, and the like.

"Alkylamino" means a radical —NHR or —NR$_2$ where each R is independently an alkyl or hydroxyalkyl group. Examples include methylamino, (1-methylethyl)amino, hydroxymethylamino, dimethylamino, methylethylamino, di(1-methyethyl)amino, (methyl)(hydroxymethyl)amino, and the like.

"Alkylene" means a linear saturated divalent hydrocarbon radical of one to six carbon atoms or a branched saturated divalent hydrocarbon radical of three to six carbon atoms. It may include a linear divalent hydrocarbon radical of one to four or one to three carbon atoms. Examples include methylene, ethylene, 2,2-dimethylethylene, propylene, 2-methylpropylene, butylene, pentylene, and the like.

"Halo" means fluoro, chloro, bromo, or iodo, such as bromo and chloro.

"Haloalkyl" means alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected, for example, from alkyl, haloalkyl, halo, nitro, cyano, cyanoalkyl, hydroxy, alkoxy, amino, and alkylamino. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, 2-pyrrolidinone-5-yl, and the derivatives thereof.

"Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

Salts, Solvates, and Hydrates:

The compounds of this invention optionally comprise salts of the compounds herein. Particular mention may be made of the pharmacologically acceptable salts of inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid. Salts with bases are also suitable, including salts with alkali metal (lithium, sodium, potassium) or calcium, aluminum, magnesium, titanium, ammonium, meglumine or guanidinium salts.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Stereoisomers:

Certain compounds of the invention contain chiral centres. Both racemic and diasteromeric mixtures, as well as the individual optical isomers isolated or synthesized, substantially free of their enantiomeric or diastereomeric partners, are all within the scope of the invention. The racemic mixtures may be separated into their individual, substantially optically pure isomers through well-known techniques, such as the separation of diastereomeric salts formed with optically active adjuncts, e.g., acids or bases followed by conversion back to the optically active substances. The desired optical isomer may be synthesized by means of stereospecific reactions, beginning with the appropriate stereoisomer of the desired starting material.

Prodrugs:

Prodrugs of the compounds of the invention are also contemplated. The terms "pro-drug" and "prodrug" are used interchangeably herein and refer to any compound which releases an active parent drug according to Formula I or Ia in vivo when such prodrug is administered to a mammalian subject. Prodrugs of a compound of Formula I or Ia are prepared by modifying one or more functional group(s) present in the compound of Formula I or Ia in such a way that the modification(s) may be cleaved in vivo to release the parent compound. Prodrugs include compounds of Formula I or Ia wherein a hydroxy, amino, carboxy or carbonyl group in a compound of Formula I or Ia is bonded to any group that may be cleaved in vivo to regenerate the free hydroxyl, or amino group, respectively. Examples of prodrugs include, but are not limited to, esters (e.g., acetate, dialkylaminoacetates, formates, phosphates, sulfates, and benzoate derivatives) and carbamates (e.g., N,N-dimethylamino carbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I or Ia, and the like, See Bundegaard, H. "Design of Prodrugs" p. 1-92, Elsevier, New York-Oxford (1985).

Pharmaceutical Formulations and Routes of Administration:

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in a conventional manner.

The compounds of the invention can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The compound of the invention including pharmaceutically acceptable salts and solvates thereof may be used on their own but will generally be administered in the form of a pharmaceutical composition in which the compound (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Uses of the Compounds:

The compounds of this invention are useful in the prophylaxis of influenza infections or treatment of existing influenza infections in animals such as duck, rodents, or swine, or in man. This includes influenza A (such as the group-1 type neuramindases including H1N1 and H5N1, and the group-2 neuraminidase including H1N2, H3N2, H7N3, H7N7, and H9N2), influenza B, and influenza C. The compounds may be especially useful in instances of drug-resistance to other influenza medications, such as adamantanes (e.g. amantadine and rimantadine) and neuraminidase inhibitors (e.g. oseltamivir and zanamivir).

The compounds disclosed herein may be used to inhibit neuraminidases. Organisms that contain neuraminidase include bacteria (*Vibrio cholerae, Clostridium perfringens,*

Streptococcus pneumoniae, and Arthrobacter sialophilus) and viruses (especially orthomyxoviruses or paramyxoviruses such as influenza virus A and B, parainfluenza virus, mumps virus, Newcastle disease virus, fowl plague virus, and Sendai virus). Inhibition of neuraminidase activity obtained from or found within any of these organisms is within the scope of this invention.

Experimental 4-(4-((3-(2-amino-4-hydroxy-6-methyl-5-pyrimidinyl)propyl)amino)phenyl)-1-chloro-3-buten-2-one (Referred to herein as NSC#89853)

This compound was obtained from the National Cancer Institute, USA. However, this compound can be prepared in accordance with Baker, B R and Jordaan, J H, *J. Med. Chem.* 1965 Jan. 8, pp. 35-41.

Cell Viability Test:

Primary human blood macrophages or MDCK cells were seeded at $2 \times 10^6$/ml in a 96-well plate for 16-24 hours. 100 uM of NSC#89853 was added to the cells. 100 uM of DMSO was added to the cells as a control. Cells were incubated at 37° C. and 5% $CO_2$ for 72 hours, and then Thiazolyl Blue Tetrazolium Bromide (MTT) was added to a final concentration of 0.1 mg/ml. After two hours, the culture supernatant was removed and each well was replenished with isopropanol. The MTT metabolic product, formazan, was dissolved in isopropanol for five minutes with shaking. The optical densities of formazan and background were measured at 560 nm and 670 nm, respectively. The degree of cytotoxicity was calculated as follows:

$(\lambda 560_{sample1} - \lambda 670_{sample1})/(\lambda 560_{DMSO} - \lambda 670_{DMSO})$ NSC#89853 does not display cytotoxicity in MDCK cells as well as in primary macrophages at 100 uM compared with those treated with DMSO.

| ASL no. | Macrophage | MDCK |
|---|---|---|
| NSC#89853 | 1.1 | 2.2 |
| DMSO | 1.0 | 1.0 |

Figure 1:
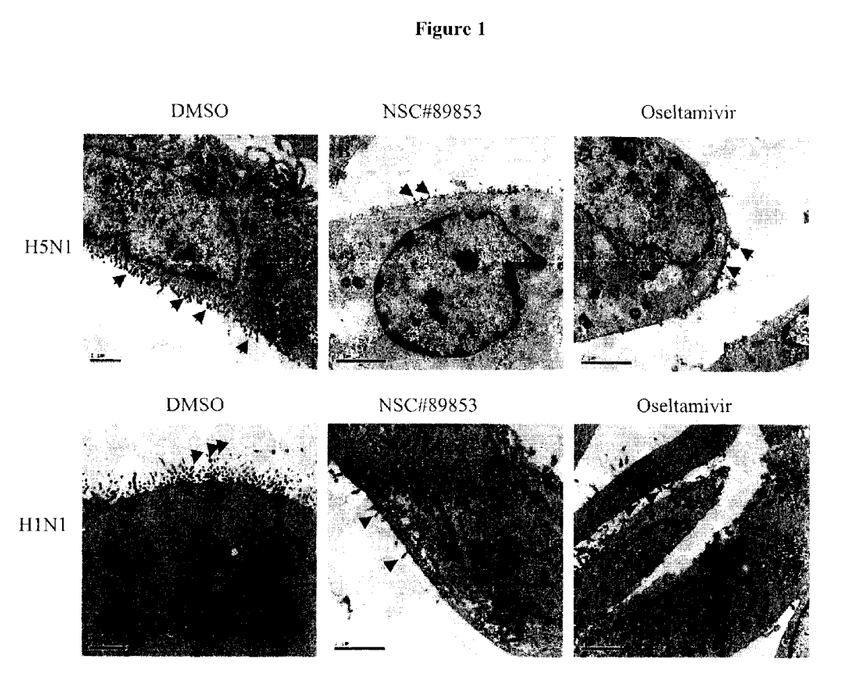
FIG. 1 shows the transmission electron microscopy of influenza virus infected cells.

Viral Infection:

Avian influenza H5N1 virus, A/Vietnam/1203/04 uM), oseltamivir (100 uM) or DMSO. At 18-hour post-infection, the cells were collected for ultrastructural examination by transmission electron microscopy. Arrows indicate the virions. Magnification: A, 14000×; B-F, 8900×.

Consistent with the results of $TCID_{50}$, the levels of H5N1 or H1N1 viruses found on the surface of MDCK cells were lower on the cells treated with NSC#89853 or oseltamivir compared with that of the DMSO-treated cells.

Figure 2:
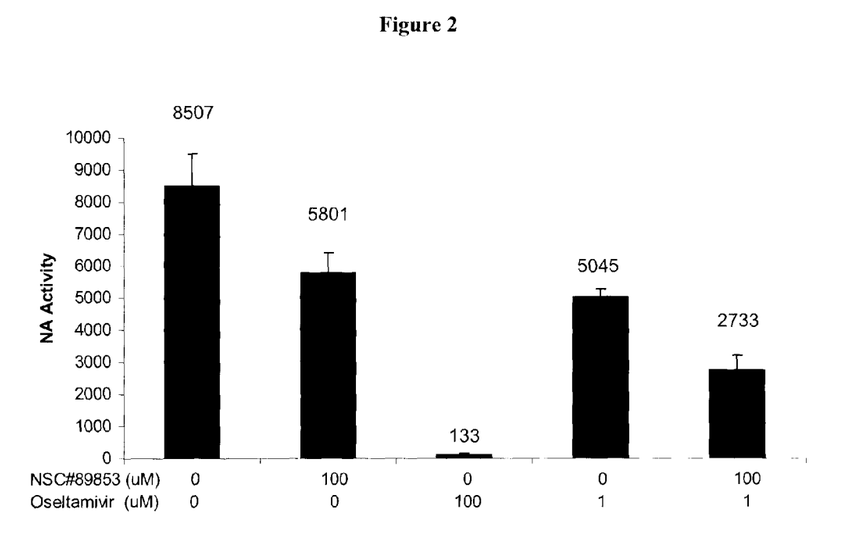
FIG. 2 shows the inhibitory effect of NSC#89853 on the group 1 neuraminidase (NA) activity.

Neuraminidase Assay:

Neuraminidase inhibitory activity was determined using the NA-Star Influenza Neuraminidase Inhibitor Resistance Detection Kit (Applied Biosystems P/N: 4374422). Briefly, 25 µl of the compounds NSC#89853 or oseltamivir at 2× the desired final concentration was added in triplicates to each well of the Star Detection 96-well microplate. H1N1 virus ($TCID_{50}=2\times10^7$/ml) was diluted five-fold with NA-Star Assay Buffer. 25 µl of the diluted virus was added per well and mixed with the compounds. The microplate was agitated and incubated at 37° C. for 20 minutes. The substrate was diluted at 1:1000 in the assay buffer immediately before use. 10 µl of diluted NA-Star Substrate was added to each well and briefly agitated on a plate shaker and incubated at room temperature for 30 minutes. 60 µl of NA-Star Accelerator was added to each well followed by immediate measurement of the chemiluminescent signal by Envison™ (Perkin Elmer). The results are shown in FIG. 2.

TABLE 2

Examples of compounds of the invention

TABLE 2-continued

Examples of compounds of the invention

TABLE 2-continued

Examples of compounds of the invention

The invention claimed is:

1. A compound consisting of:

-continued

-continued

2. A pharmaceutical composition comprising the compound of claim 1, in admixture with a suitable pharmaceutically acceptable diluent or carrier.

3. The pharmaceutical composition of claim 2, in admixture with a medication for the treatment of influenza.

4. The pharmaceutical composition of claim 3, wherein the medication for the treatment of influenza is oseltamivir, zanamivir, amantadine, or rimantadine.

5. A method for treating influenza in a subject, comprising administering to said subject an effective amount of the compound of claim 1, wherein the influenza is influenza type A or influenza type B.

6. A method for treating influenza in a subject, comprising administering to said subject an effective amount of 4-(4-((3-(2-amino-4-hydroxy-6-methyl-5-pyrimidinyl)propyl)amino)phenyl)-1-chloro-3-buten-2-one, wherein the influenza is influenza type A or influenza type B.

7. The method of claim 5, wherein the influenza is influenza type A.

8. The method of claim 5, wherein the influenza is type A group-1.

9. The method of claim 5, wherein the influenza is type A group-2.

10. The method of claim 5, wherein the influenza is H1N1, H1N2, H3N2, H5N1, H9N2, H7N3, or H7N7.

11. The method of claim 5, wherein the influenza is Type A H5N1 influenza.

12. The method of claim 5, wherein the influenza is Type A H1N1 influenza.

13. The method of claim 5, wherein the influenza is a drug-resistant strain of influenza.

14. The method of claim 13, wherein drug-resistant strain is resistant to oseltamivir or zanamivir.

15. A method for inhibiting endogenous mammalian neuraminidases in a subject, comprising administering to said subject an effective amount of the compound of claim 1.

16. A method for inhibiting endogenous mammalian neuraminidases in a subject, comprising administering to said subject an effective amount of 4-(4-((3-(2-amino-4-hydroxy-6-methyl-5-pyrimidinyl)propyl)amino)phenyl)-1-chloro-3-buten-2-one.

17. The method of claim 6, wherein the influenza is influenza type A.

18. The method of claim 6, wherein the influenza is type A group-1.

19. The method of claim 6, wherein the influenza is type A group-2.

20. The method of claim 6, wherein the influenza is H1N1, H1N2, H3N2, H5N1, H9N2, H7N3, or H7N7.

21. The method of claim 6, wherein the influenza is Type A H5N1 influenza.

22. The method of claim 6, wherein the influenza is Type A H1N1 influenza.

23. The method of claim 6, wherein the influenza is a drug-resistant strain of influenza.

24. The method of claim 23, wherein the drug-resistant strain is resistant to oseltamivir or zanamivir.

* * * * *